(12) United States Patent
Awau

(10) Patent No.: US 9,924,857 B2
(45) Date of Patent: Mar. 27, 2018

(54) ENDOSCOPE REPROCESSOR

(71) Applicant: OLYMPUS CORPORATION, Tokyo (JP)

(72) Inventor: Yumiko Awau, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/386,915

(22) Filed: Dec. 21, 2016

(65) Prior Publication Data

US 2017/0100027 A1    Apr. 13, 2017

Related U.S. Application Data

(63) Continuation of application No. PCT/JP2016/060420, filed on Mar. 30, 2016.

(30) Foreign Application Priority Data

May 27, 2015   (JP) .................. 2015-107808

(51) Int. Cl.
*A61B 1/12*         (2006.01)
*A61L 2/18*         (2006.01)
(Continued)

(52) U.S. Cl.
CPC ............... *A61B 1/123* (2013.01); *A61L 2/18* (2013.01); *B08B 3/08* (2013.01); *B08B 3/102* (2013.01);
(Continued)

(58) Field of Classification Search
CPC ....... A61B 1/123; A61L 2/18; A61L 2202/24; B08B 3/08; B08B 3/102; B08B 9/023; B08B 9/0328; G01N 21/01
(Continued)

(56) References Cited

U.S. PATENT DOCUMENTS

| | | | |
|---|---|---|---|
| 2009/0062610 A1 | 3/2009 | Williams | |
| 2009/0087566 A1* | 4/2009 | Kimura | ...................... B08B 3/08 427/299 |
| 2009/0090398 A1* | 4/2009 | Onishi | ................... A61B 1/122 134/167 C |

FOREIGN PATENT DOCUMENTS

| | | |
|---|---|---|
| CN | 101209197 A | 7/2008 |
| CN | 101399183 A | 4/2009 |

(Continued)

OTHER PUBLICATIONS

International Search Report dated Jun. 28, 2016 issued in PCT/JP2016/060420.
(Continued)

*Primary Examiner* — Levon J Shahinian
(74) *Attorney, Agent, or Firm* — Scully, Scott, Murphy & Presser, P.C.

(57) ABSTRACT

An endoscope reprocessor includes a medicinal solution tank configured to store a medicinal solution; a first detachable portion provided in the medicinal solution tank and configured to detachably hold the concentration meter such that a measuring surface of the concentration meter is placed in the medicinal solution tank; a preserving fluid tank configured to store a preserving fluid of the concentration meter; and a second detachable portion provided in the preserving fluid tank and configured to detachably hold the concentration meter such that the measuring surface of the concentration meter is placed in the preserving fluid tank.

6 Claims, 13 Drawing Sheets

(51) Int. Cl.
*B08B 3/08* (2006.01)
*B08B 3/10* (2006.01)
*B08B 9/023* (2006.01)
*B08B 9/032* (2006.01)
*G01N 21/01* (2006.01)

(52) U.S. Cl.
CPC ............ *B08B 9/023* (2013.01); *B08B 9/0328* (2013.01); *G01N 21/01* (2013.01); *A61L 2202/24* (2013.01)

(58) Field of Classification Search
USPC ...... 134/61, 94.1, 95.1, 99.1, 105, 107, 109, 134/110
See application file for complete search history.

(56) References Cited

FOREIGN PATENT DOCUMENTS

| | | |
|---|---|---|
| JP | 2006-126046 A | 5/2006 |
| JP | 2010-057792 A | 3/2010 |
| JP | 2010-119592 A | 6/2010 |
| JP | 2013-064702 A | 4/2013 |

OTHER PUBLICATIONS

Extended Supplementary European Search Report dated Jan. 18, 2018 in European Patent Application No. 16 79 9673.5.

\* cited by examiner

ENDOSCOPE REPROCESSOR

CROSS REFERENCE TO RELATED APPLICATION

This application is a continuation application of PCT/JP2016/060420 filed on Mar. 30, 2016 and claims benefit of Japanese Application No. 2015-107808 filed in Japan on May 27, 2015, the entire contents of which are incorporated herein by this reference.

BACKGROUND OF THE INVENTION

1. Field of the Invention

The present invention relates to an endoscope reprocessor configured to apply a reprocessing process using a medicinal solution to an endoscope.

2. Description of the Related Art

A reprocessing process including a cleaning process and a disinfecting process is applied after use to an endoscope used in a medical field. Also, an endoscope reprocessor configured to automatically perform a reprocessing process for the endoscope is known. An endoscope reprocessor is equipped with a medicinal solution tank configured to store a medicinal solution used in the reprocessing process. Also, a concentration meter, such as disclosed in Japanese Patent Application Laid-Open Publication No. 2006-126046, configured to measure concentration of the medicinal solution is sometimes used to judge whether a medicinal solution for use in a reprocessing process is usable.

The concentration meter takes a longer waiting time from when a measuring surface contacts a medicinal solution to when correct measurement results become available if the measuring surface contacting the medicinal solution during concentration measurement is in a dry state than when the measuring surface is in a wet state. To reduce the waiting time, a concentration meter disclosed in Japanese Patent Application Laid-Open Publication No. 2006-126046 moisturizes the measuring surface by pressing the measuring surface against a spongy porous material moistened by a preserving fluid.

SUMMARY OF THE INVENTION

An endoscope reprocessor according to one aspect of the invention includes a medicinal solution tank configured to store a medicinal solution; a first detachable portion provided in the medicinal solution tank and configured to detachably hold a concentration meter such that a measuring surface of the concentration meter is placed in the medicinal solution tank; a preserving fluid tank configured to store a preserving fluid of the concentration meter; and a second detachable portion provided in the preserving fluid tank and configured to detachably hold the concentration meter such that the measuring surface of the concentration meter is placed in the preserving fluid tank.

DETAILED DESCRIPTION OF THE PREFERRED EMBODIMENT(S)

Figure 1:
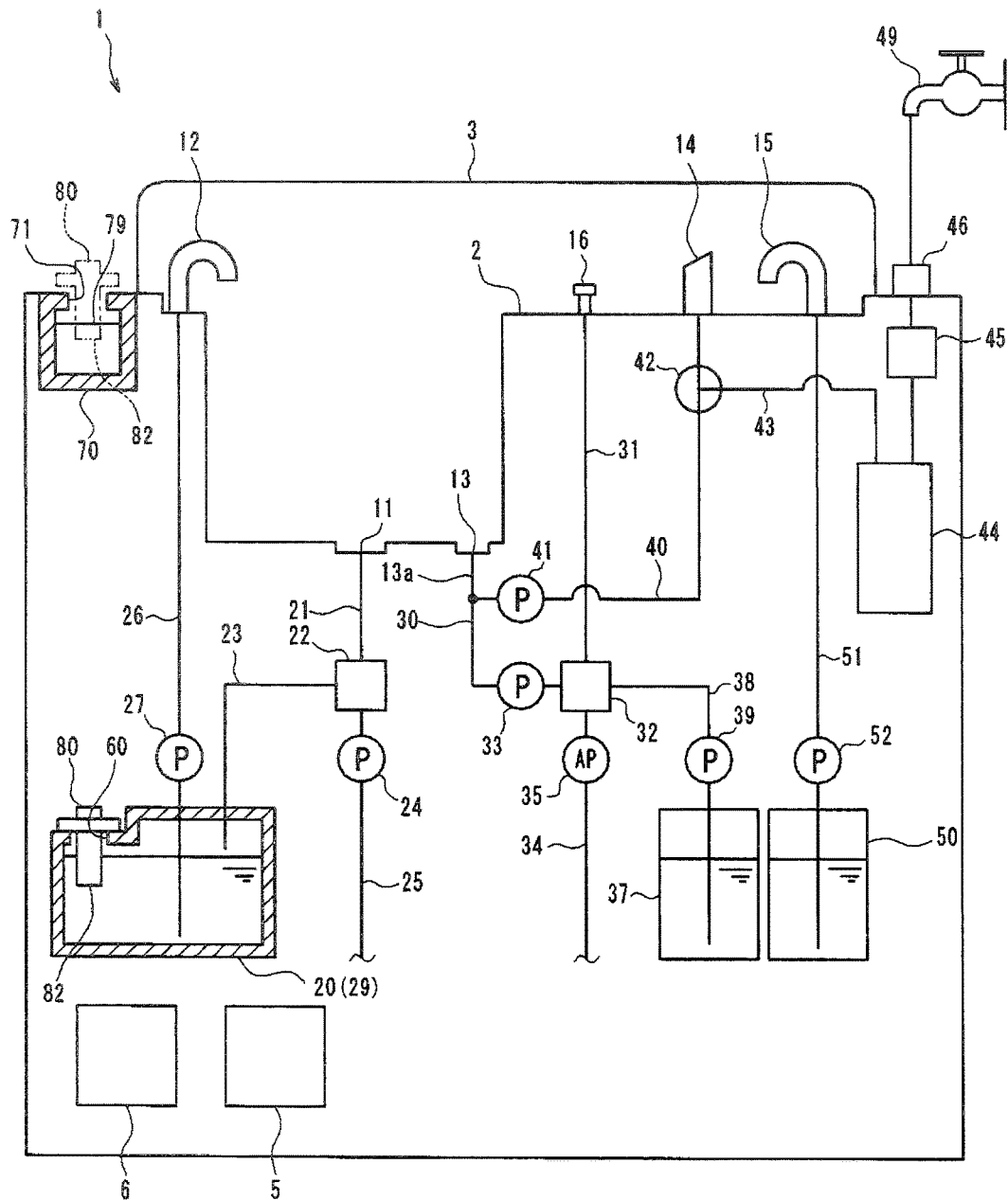
FIG. 1 is a diagram showing a schematic configuration of an endoscope reprocessor according to a first embodiment.

Preferred embodiments of the present invention will be described below with reference to the drawings. In the individual drawings referred to in the following description, to make each component large enough to be recognized, scaling is varied from component to component, and thus it should be noted that the present invention is not limited to quantities of the components, shapes of the components, size ratios of the components, and relative positional relationships of the individual components shown in the drawings.

(First Embodiment)

An example of an embodiment of the present invention will be described below. An endoscope reprocessor 1 shown in FIG. 1 is an apparatus configured to perform a reprocessing process on an endoscope. The reprocessing process as referred to herein is not particularly limited, and may be any of a rinsing process using water, a cleaning process for removing contaminants such as organic matter, a disinfecting process for neutralizing predetermined microbes, a sterilization process for eliminating or killing all microbes, and a combination of these processes.

Note that in the following description, the term "above" corresponds to an upward direction along a direction of gravity while the term downward corresponds to a downward direction along a direction of gravity. Also, in the following description, the terms upward and "low" represent height relations along the direction of gravity.

The endoscope reprocessor 1 includes a control unit 5, a power supply unit 6, a treatment tank 2, a medicinal solution tank 20, a first detachable portion 60, a preserving fluid tank 70, and a second detachable portion 71.

The control unit 5 can include a central processing unit (CPU), a storage device (RAM), an auxiliary storage device, an input-output device, and a power control device, and is configured to control operation of each part of the endoscope reprocessor 1 based on a predetermined program. In the following description, operation of individual components included in the endoscope reprocessor 1 is controlled by the control unit 5 even if there is no particular mention to that effect.

The power supply unit 6 supplies electric power to various parts of the endoscope reprocessor 1. The power supply unit 6 distributes electric power obtained from an outside source, such as a commercial power source, to the various parts. Note that the power supply unit 6 may be equipped with an electrical generator or battery.

Having a concave shape provided with an opening portion which opens, the treatment tank 2 is capable of storing a liquid inside. A non-illustrated endoscope can be placed in the treatment tank 2. According to the present embodiment, as an example, upper part of the treatment tank 2 is provided with a cover 3 configured to open and close the opening portion of the treatment tank 2. When a reprocessing process is applied to the endoscope in the treatment tank 2, the opening portion of the treatment tank 2 is closed by the cover 3.

The treatment tank 2 is provided with a medicinal solution nozzle 12 and a drain hole 11.

The medicinal solution nozzle 12 is an opening portion communicating with the medicinal solution tank 20 through a medicinal solution conduit 26. The medicinal solution tank 20 stores a medicinal solution. The type of the medicinal solution stored in the medicinal solution tank 20 is not particularly limited, but according to the present embodiment, as an example, the medicinal solution is a disinfecting solution used for the disinfecting process. However, the present invention is not limited to this, and a cleaning solution used for a cleaning process, a high volatile solution used for a drying process, or the like can be selected appropriately as a medicinal solution according to purpose.

Also, according to the present embodiment, as an example, when the endoscope reprocessor 1 is not operating using a medicinal solution, the medicinal solution tank 20 stores the medicinal solution contained in the endoscope reprocessor 1. That is, according to the present embodiment, the medicinal solution tank 20 also serves as a medicinal solution recovery unit 29 configured to recover the medicinal solution which has come into contact with the endoscope in the treatment tank 2 and store the recovered medicinal solution. In the following description, the medicinal solution tank 20 and medicinal solution recovery unit 29, when not distinguished from each other, are simply referred to as the medicinal solution tank 20.

Note that the medicinal solution tank 20 may be provided separately from the medicinal solution recovery unit 29. When the medicinal solution tank 20 is configured to be separate from the medicinal solution recovery unit 29, the medicinal solution tank 20 may be smaller in capacity than the medicinal solution recovery unit 29.

The medicinal solution conduit 26 is provided with a medicinal solution pump 27. When the medicinal solution pump 27 is operated, the medicinal solution in the medicinal solution tank 20 is transferred to the treatment tank 2. The medicinal solution tank 20 is provided with a first detachable portion 60 described later.

The drain hole 11 is an opening portion provided in a lowermost place in the treatment tank 2. The drain hole 11 is connected to a discharge conduit 21. The discharge conduit 21 causes the drain hole 11 and a selector valve 22 to communicate with each other. The selector valve 22 is connected with a recovery conduit 23 and disposal conduit 25. The selector valve 22 can switch among a state in which the discharge conduit 21 is closed, a state in which the discharge conduit 21 and recovery conduit 23 communicate with each other, and a state in which the discharge conduit 21 and disposal conduit 25 communicate with each other.

The recovery conduit 23 causes the medicinal solution tank 20 and selector valve 22 to communicate with each other. Also, the disposal conduit 25 is provided with a discharge pump 24. The disposal conduit 25 is connected to drainage facilities used to receive a liquid discharged from the endoscope reprocessor 1.

If the selector valve 22 is closed, a liquid can be stored in the treatment tank 2. Also, when a medicinal solution is stored in the treatment tank 2, if the selector valve 22 is set such that the discharge conduit 21 and recovery conduit 23 communicate with each other, the medicinal solution is transferred from the treatment tank 2 to the medicinal solution tank 20. Also, with the selector valve 22 is set such that the discharge conduit 21 and disposal conduit 25 communicate with each other, when the discharge pump 24 is started to operate, the liquid in the treatment tank 2 is sent out to the drainage facilities through the disposal conduit 25.

Also, the treatment tank 2 is provided with a circulation port 13, a circulation nozzle 14, a cleaning solution nozzle 15, and an endoscope connecting portion 16.

The circulation port 13 is an opening portion provided near a bottom face of the treatment tank 2. The circulation port 13 communicates with a circulation conduit 13*a*. The circulation conduit 13*a* branches into two conduits: an endoscope circulation conduit 30 and a treatment tank circulation conduit 40.

The endoscope circulation conduit 30 causes the circulation conduit 13*a* and a channel valve 32 described later to communicate with each other. The endoscope circulation conduit 30 is provided with a circulating pump 33. The circulating pump 33, when operated, transfers the fluid in the endoscope circulation conduit 30 toward the channel valve 32.

The channel valve 32 is connected with an intake conduit 34, an alcohol conduit 38, and an endoscope connection conduit 31 in addition to the endoscope circulation conduit 30 described above. The channel valve 32 selectively causes the endoscope connection conduit 31 to communicate with any one of the endoscope circulation conduit 30, intake conduit 34, and alcohol conduit 38.

The intake conduit 34 is open to the atmosphere at one end portion, and connected to the channel valve 32 at the other end portion. Note that although not illustrated, a filter is provided at the one end portion of the intake conduit 34 to filter gas passing through the filter. An air pump 35 is provided on the intake conduit 34, and when operated, transfers the gas in the intake conduit 34 toward the channel valve 32.

The alcohol conduit 38 causes an alcohol tank 37 and a channel valve 32 to communicate with each other, where the alcohol tank 37 stores an ethanol water solution. An alcohol pump 39 is provided on the alcohol conduit 38, and when operated, transfers an ethanol water solution in the alcohol tank 37 toward the channel valve 32.

The endoscope connection conduit 31 causes the endoscope connecting portion 16 provided in the treatment tank 2 and the channel valve 32 to communicate with each other.

When a liquid is stored in the treatment tank 2, if the circulating pump 33 is started to operate with the channel valve 32 set such that the endoscope connection conduit 31 and endoscope circulation conduit 30 communicate with each other, the liquid in the treatment tank 2 is sent out from the endoscope connecting portion 16 via the circulation port 13, circulation conduit 13a, endoscope circulation conduit 30, and endoscope connection conduit 31.

Also, with the channel valve 32 set such that the endoscope connection conduit 31 and intake conduit 34 communicate with each other, when the air pump 35 is started to operate, air is sent out from the endoscope connecting portion 16. Also, with the channel valve 32 set such that the endoscope connection conduit 31 and alcohol conduit 38 communicate with each other, when the alcohol pump 39 is started to operate, the ethanol water solution in the alcohol tank 37 is sent out from the endoscope connecting portion 16.

The endoscope connecting portion 16 is connected to a pipe sleeve provided on the endoscope via a no-illustrated endoscope tube. Thus, the liquid and gas sent out from the endoscope connecting portion 16 are sent into the pipe sleeve of the endoscope.

The treatment tank circulation conduit 40 causes the circulation conduit 13a and circulation nozzle 14 to communicate with each other. The circulation nozzle 14 is an opening portion provided in the treatment tank 2. The treatment tank circulation conduit 40 is provided with a circulation pump 41.

Also, a three-way valve 42 is provided between the circulation pump 41 of the treatment tank circulation conduit 40 and the circulation nozzle 14. The three-way valve 42 is connected with a water supply conduit 43. The three-way valve 42 switches between a state in which the circulation nozzle 14 and treatment tank circulation conduit 40 communicate with each other and a state in which the circulation nozzle 14 and water supply conduit 43 communicate with each other.

The water supply conduit 43 causes the three-way valve 42 and a water supply source connecting portion 46 to communicate with each other. The water supply conduit 43 is provided with a water introduction valve 45 configured to open and close the water supply conduit 43 and a water filter 44 configured to filter water. The water supply source connecting portion 46 is connected, for example, through a tube to a water supply source 49 such as a tap water system configured to send out water.

When a liquid is stored in the treatment tank 2, if the circulation pump 41 is started to operate with the three-way valve 42 set such that the circulation nozzle 14 and treatment tank circulation conduit 40 communicate with each other, the liquid in the treatment tank 2 is discharged from the circulation nozzle 14 by passing through the circulation port 13, circulation conduit 13a, and treatment tank circulation conduit 40. Also, when the water introduction valve 45 is opened with the three-way valve 42 set such that the circulation nozzle 14 and water supply conduit 43 communicate with each other, water supplied from the water supply source 49 is discharged through the circulation nozzle 14. The liquid discharged through the circulation nozzle 14 is introduced into the treatment tank 2.

The cleaning solution nozzle 15 is an opening portion communicating with a cleaning solution tank 50 configured to store a cleaning solution, through a cleaning solution conduit 51. The cleaning solution is used for a cleaning process. The cleaning solution conduit 51 is provided with a cleaning solution pump 52. When the cleaning solution pump 52 is operated, the cleaning solution in the cleaning solution tank 50 is transferred to the treatment tank 2.

Figure 2:
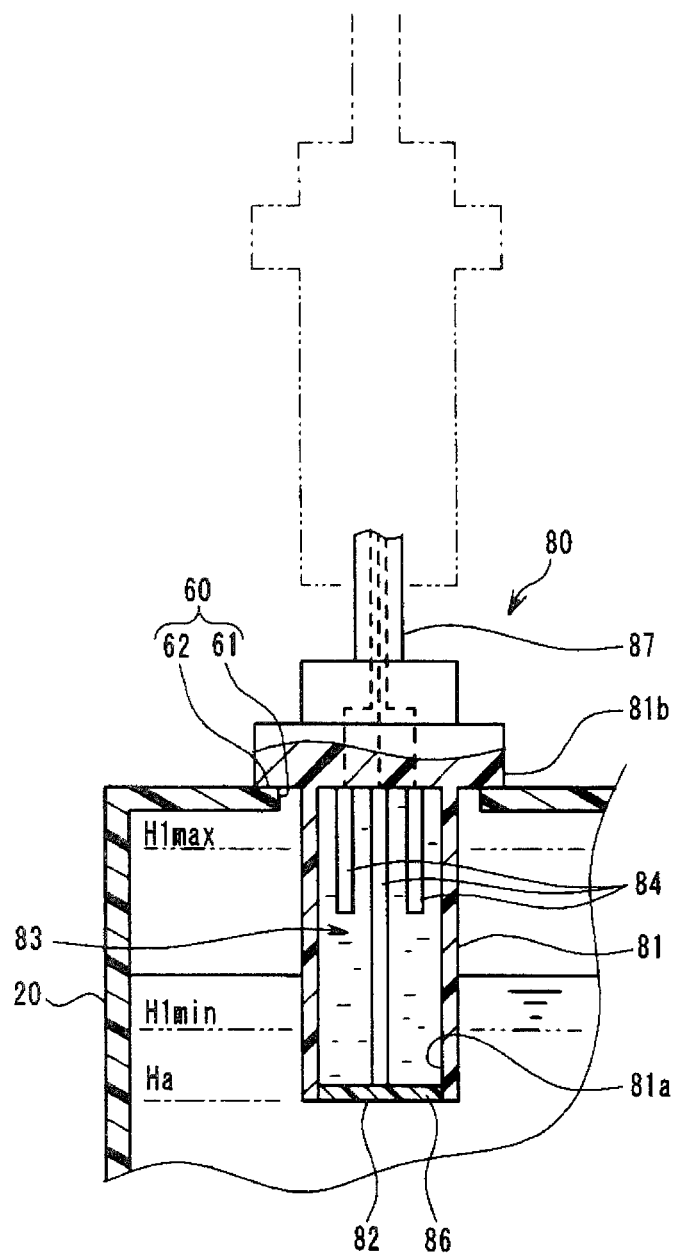
FIG. 2 is a sectional view of a first detachable portion and a concentration meter according to the first embodiment.

FIG. 2 is a sectional view of the first detachable portion 60. The first detachable portion 60 is provided on the medicinal solution tank 20. The first detachable portion 60 holds a concentration meter 80 such that a measuring surface 82 of the concentration meter 80 will be placed in the medicinal solution tank 20. Also, the first detachable portion 60 holds the concentration meter 80 detachably.

The concentration meter 80 measures a concentration of the medicinal solution contacting the measuring surface 82. The concentration meter 80 may be either designed to be included in the endoscope reprocessor 1 and electrically connected to the control unit 5 or designed to operate as a separate unit without being included in the endoscope reprocessor 1. According to the present embodiment, as an example, the concentration meter 80 is electrically connected to the control unit 5 and information on concentration measurement results of the medicinal solution measured by the concentration meter 80 is inputted to the control unit 5.

The measuring surface 82 is part of an outer surface of a measuring unit 81. The measuring unit 81 is a container-shaped member provided with an opening portion 81a. The opening portion 81a is sealed by an osmosis membrane 86. A content fluid 83 is enclosed inside the opening portion 81a of the measuring unit 81.

The measuring surface 82 is that surface of the osmosis membrane 86 which is opposite an area touching the content fluid 83. The osmosis membrane 86 allows a particular ion of the medicinal solution contacting the measuring surface 82 to be transmitted into the content fluid 83. That is, ion concentration in the content fluid 83 changes with ion concentration in the medicinal solution contacting the measuring surface 82.

According to the present embodiment, as an example, the measuring unit 81 has a rod-like external shape and is provided with the measuring surface 82 at one end. Note that the measuring surface 82 may be provided on a side face of the measuring unit 81.

In the measuring unit 81, a pair of electrodes 84 are disposed in the content fluid 83, being spaced away from each other. The pair of electrodes 84 are connected to a non-illustrated control device via an electrical cable 87. The electrical cable 87 may be detachable from the measuring unit 81. Note that the control device of the measuring unit 81 may be configured integrally with the measuring unit 81.

With the pair of electrodes 84 immersed in the content fluid 83, the concentration meter 80 measures changes in a potential difference existing between the pair of electrodes 84 or changes in a value of current flowing between the pair of electrodes 84. Then, based on resulting measured values, the concentration meter 80 measures the concentration of the medicinal solution contacting the measuring surface 82. A principle and configuration of such concentration measurements with the concentration meter 80 are well-known, and thus detailed description of the measurements will be omitted.

The first detachable portion 60 holds the measuring unit 81 of the above-mentioned concentration meter 80 with the measuring surface 82 placed in the medicinal solution tank 20. The first detachable portion 60 may be designed to hold the measuring unit 81 with the entire measuring unit 81 placed in the medicinal solution tank 20 or may be designed to hold the measuring unit 81 such that only a region containing the measuring surface 82, which is part of the measuring unit 81, will be placed in the medicinal solution tank 20.

The first detachable portion 60 according to the present embodiment includes an insertion hole 61 and a holding portion 62.

The insertion hole 61 is an opening portion configured to cause an outer space and inner space of the medicinal solution tank 20 to communicate with each other. The insertion hole 61 is shaped to allow that part of the measuring unit 81 on which the measuring surface 82 is provided to be inserted from outside the medicinal solution tank 20. According to the present embodiment, as an example, the insertion hole 61 is provided above a height H1max corresponding to the highest liquid level of the medicinal solution in the medicinal solution tank 20.

Note that the insertion hole 61 may be provided below the height H1max if configured to be able to be sealed, with the measuring unit 81 inserted inside. In that case, a member used to seal the insertion hole 61 with the measuring unit 81 inserted inside may be either integral with, or separate from, the measuring unit 81.

The holding portion 62 holds the measuring unit 81 inserted into the medicinal solution tank 20 through the insertion hole 61, at a predetermined position. With the measuring unit 81 held by the holding portion 62, the measuring surface 82 is placed at a predetermined height Ha in the medicinal solution tank 20.

The predetermined height Ha is lower than the height H1max in the medicinal solution tank 20. According to the present embodiment, as an example, the predetermined height Ha is lower than a height H1min of the liquid level of the medicinal solution in the medicinal solution tank 20 when a minimum volume of the medicinal solution necessary for the endoscope reprocessor 1 in order to perform a reprocessing process is stored in the medicinal solution tank 20, which is the medicinal solution recovery unit 29.

Therefore, with the endoscope reprocessor 1 according to the present embodiment, in a state in which the concentration meter 80 is held by the first detachable portion 60, if the medicinal solution is stored until reaching a position higher than the predetermined height Ha in the medicinal solution tank 20, the measuring surface 82 contacts the medicinal solution, enabling an operation of measuring the concentration of the medicinal solution using the concentration meter 80.

According to the present embodiment, the medicinal solution tank 20 also serves as the medicinal solution recovery unit 29, and since the predetermined height Ha is lower than the height H1min, when all the medicinal solution is recovered in the medicinal solution tank 20, the measuring surface 82 of the concentration meter 80 held by the first detachable portion 60 contacts the medicinal solution.

Preferably the endoscope reprocessor 1 includes a liquid level sensor configured to detect whether or not the medicinal solution has been stored until reaching a position higher than the predetermined height Ha in the medicinal solution tank 20.

Note that unlike the present embodiment, when the medicinal solution tank 20 and medicinal solution recovery unit 29 are provided as separate members, the predetermined height Ha is established irrespective of the height H1min.

The configuration in which the holding portion 62 holds the measuring unit 81 at a predetermined position is not particularly limited as long as the contact between the measuring surface 82 and medicinal solution is not obstructed. According to the present embodiment, as an example, as shown in FIG. 2, the holding portion 62 abuts the measuring unit 81 inserted into the insertion hole 61 from outside the medicinal solution tank 20 and thereby limits insertion depth of the measuring unit 81 into the insertion hole 61. According to the present embodiment, when the measuring unit 81 is inserted into the insertion hole 61 by a predetermined distance, the holding portion 62 abuts a convex portion 81*b* projecting from a lateral portion of the measuring unit 81 and thereby limits a further advance of the measuring unit 81 into the insertion hole 61. Then, in a state in which the measuring unit 81 is inserted in the insertion hole 61 by the predetermined distance, the measuring surface 82 is placed at the predetermined height Ha in the medicinal solution tank 20.

Note that the configuration of the holding portion 62 is not limited to that of the present embodiment. For example, the holding portion 62 may surround the measuring unit 81 with a netlike member provided with apertures configured to transmit the medicinal solution and may be designed to hold the measuring unit 81 at a predetermined position in the medicinal solution tank 20.

Also, the holding portion 62 may be configured to display holding power to fix the measuring unit 81 to a predetermined position. The holding portion 62 may be configured, for example, to pinch the measuring unit 81 by an elastic force of a spring member or the like or the holding portion 62 may be configured, for example, to fasten the measuring unit 81 at a predetermined position using a screw mechanism. If the holding portion 62 is configured to display holding power to fix the measuring unit 81 to a predetermined position it is possible to prevent the measuring unit 81 from moving due to pressure changes in the medicinal solution tank 20 caused by changes in volume of the medicinal solution stored in the medicinal solution tank 20 or due to buoyancy acting on the measuring unit 81.

Preferably the first detachable portion 60 includes a detection unit configured to detect whether or not the measuring unit 81 is held such that the measuring surface 82 will be placed at a predetermined position and output a detection result to the control unit 5.

Figure 3:
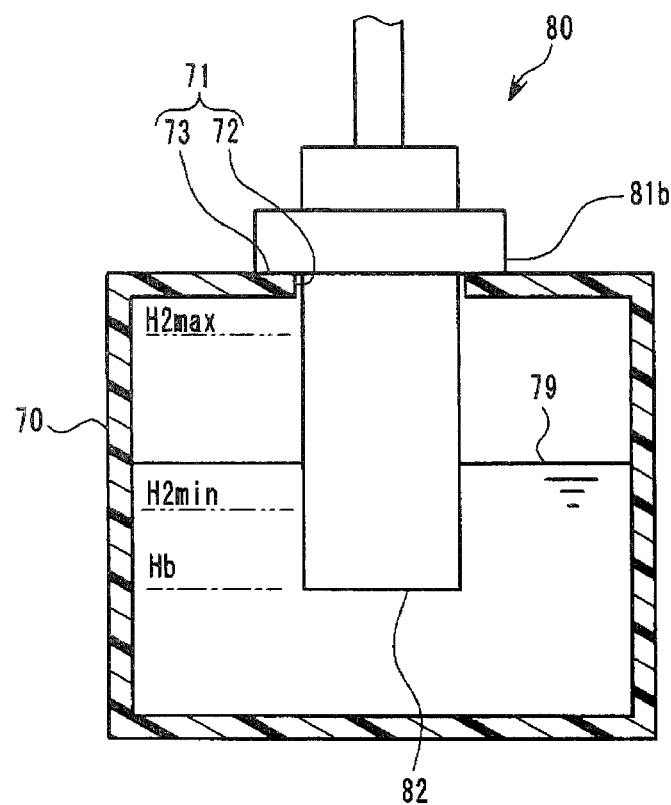
FIG. 3 is a sectional view of a preserving fluid tank and a second detachable portion according to the first embodiment.

FIG. 3 is a sectional view of the preserving fluid tank 70 and second detachable portion 71. The preserving fluid tank 70 stores a preserving fluid.

The type of preserving fluid 79 is not particularly limited, and may be water, a cleaning solution, a disinfecting solution, a high polarity liquid, or the like. For example, when a high polarity liquid is used as the preserving fluid 79, preferably the preserving fluid 79 is a liquid having a solubility parameter of 20 or above. Examples of liquids with a solubility parameter of 20 or above include water, ethanol, and acetone.

The preserving fluid tank 70 may be a member independent of other tanks and conduits provided on the endoscope reprocessor 1 or may be a member which also serves as at least part of the other tanks and conduits provided on the endoscope reprocessor 1.

According to the present embodiment, as an example, the preserving fluid tank 70 is provided independently of the other tanks and conduits provided on the endoscope reprocessor 1.

The preserving fluid tank 70 is provided with the second detachable portion 71. The second detachable portion 71 holds the concentration meter 80 such that the measuring surface 82 of the concentration meter 80 will be placed in the preserving fluid tank 70. Also, the second detachable portion 71 holds the concentration meter 80 detachably. Note that the concentration meter 80 is the one held by the first detachable portion 60 described above.

The second detachable portion 71 according to the present embodiment includes an insertion hole 72 and a holding portion 73.

The insertion hole 72 is an opening portion configured to cause an outer space and inner space of the preserving fluid tank 70 to communicate with each other. The insertion hole 72 is shaped to allow that part of the measuring unit 81 on which the measuring surface 82 is provided to be inserted from outside the preserving fluid tank 70. According to the present embodiment, as an example, the insertion hole 72 is provided above a height H2max corresponding to the highest liquid level of the preserving fluid 79 in the preserving fluid tank 700.

Note that the insertion hole 72 may also serve as an opening portion used to inject the preserving fluid 79 into the preserving fluid tank 70. Also, the insertion hole 72 may be provided lower than the height H2max if configured to be able to be sealed, with the measuring unit 81 inserted inside. In that case, a member used to seal the insertion hole 72 with the measuring unit 81 inserted inside may be either integral with, or separate from, the measuring unit 81.

The holding portion 73 holds the measuring unit 81 inserted into the preserving fluid tank 70 through the insertion hole 72, at a predetermined position. With the measuring unit 81 held by the holding portion 73, the measuring surface 82 is placed at a predetermined height Hb in the preserving fluid tank 70.

The predetermined height Hb is lower than a minimum liquid level height H2min established beforehand in the preserving fluid tank 70. Liquid level height of the preserving fluid 79 stored in the preserving fluid tank 70 is monitored by a user visually or by an automatic measurement device and manually or automatically kept higher than the minimum liquid level height H2min.

Thus, with the endoscope reprocessor 1 according to the present embodiment, in a state in which the concentration meter 80 is held by the second detachable portion 71, the measuring surface 82 is submerged in the preserving fluid 79.

The configuration in which the holding portion 73 holds the measuring unit 81 at a predetermined position is not particularly limited as long as the contact between the measuring surface 82 and preserving fluid 79 is not obstructed. According to the present embodiment, as an example, as shown in FIG. 3, the holding portion 73 abuts the measuring unit 81 inserted into the insertion hole 72 from outside the preserving fluid tank 70 and thereby limits insertion depth of the measuring unit 81 into the insertion hole 72. According to the present embodiment, when the measuring unit 81 is inserted into the insertion hole 72 by a predetermined distance, the holding portion 73 abuts the convex portion 81b projecting from the lateral portion of the measuring unit 81 and thereby limits a further advance of the measuring unit 81 into the insertion hole 72. Then, in a state in which the measuring unit 81 is inserted in the insertion hole 72 by the predetermined distance, the measuring surface 82 is placed at the predetermined height Hb in the preserving fluid tank 70.

Note that the configuration of the holding portion 73 is not limited to that of the present embodiment. For example, the holding portion 73 may surround the measuring unit 81 with a netlike member provided with apertures configured to transmit the medicinal solution and may be designed to hold the measuring unit 81 at a predetermined position in the preserving fluid tank 70.

Also, the holding portion 73 may be configured to display holding power to fix the measuring unit 81 to a predetermined position. The holding portion 73 may be configured, for example, to pinch the measuring unit 81 by an elastic force of a spring member or the like or the holding portion 73 may be configured, for example, to fasten the measuring unit 81 at a predetermined position using a screw mechanism. If the holding portion 73 is configured to display holding power to fix the measuring unit 81 to a predetermined position it is possible to prevent the measuring unit 81 from moving due to pressure changes in the preserving fluid tank 70 or due to buoyancy acting on the measuring unit 81.

The second detachable portion 71 may include a detection unit configured to detect whether or not the measuring unit 81 is held such that the measuring surface 82 will be placed at a predetermined position and output a detection result to the control unit 5.

As described above, the endoscope reprocessor 1 according to the present embodiment includes the medicinal solution tank 20 configured to store a medicinal solution; the first detachable portion 60 configured to detachably hold the concentration meter 80 such that the measuring surface 82 of the concentration meter 80 is placed in the medicinal solution tank 20; the preserving fluid tank 70 configured to store a preserving fluid 79; and the second detachable portion 71 configured to detachably hold the concentration meter 80 such that the measuring surface 82 of the concentration meter 80 is placed in the preserving fluid tank 70.

In performing a reprocessing process for the endoscope, the endoscope reprocessor 1 according to the present embodiment causes the first detachable portion 60 to hold the measuring unit 81 of the concentration meter 80. Therefore, during a reprocessing process for the endoscope, the concentration of the medicinal solution in the medicinal solution tank 20 is measured by the concentration meter 80. Then, based on concentration measurement results of the medicinal solution, the control unit 5 judges whether the medicinal solution is usable.

During the reprocessing process for the endoscope, the medicinal solution is recovered in the medicinal solution tank 20 after use in the treatment tank 2. Thus, the measuring surface 82 of the concentration meter 80 is kept in a wet state which allows concentration measurements to be taken promptly.

Then, in the endoscope reprocessor 1 according to the present embodiment, if a state in which no medicinal solution is present in the medicinal solution tank 20 is kept for a relatively long period, the measuring unit 81 of the concentration meter 80 is caused to be held by the second detachable portion 71.

Here, the case where a state in which no medicinal solution is present in the medicinal solution tank 20 is kept for a relatively long period is, for example, a case in which the medicinal solution is removed from the medicinal solution tank 20 to replace the medicinal solution. As the measuring unit 81 is caused to be held by the second detachable portion 71, the measuring surface 82 of the concentration meter 80 is submerged in the preserving fluid 79 in the preserving fluid tank 70, the measuring surface 82 is kept in a wet state which allows concentration measurements to be taken without delay.

Then, after the medicinal solution tank 20 is filled with the medicinal solution, the measuring unit 81 is caused to be held by the first detachable portion 60. In so doing, since the measuring surface 82 of the concentration meter 80 is kept sufficiently wet with the preserving fluid 79, concentration measurements of the medicinal solution can be taken by the concentration meter 80 without delay.

In this way, the endoscope reprocessor 1 according to the present embodiment can keep the measuring surface 82 of the concentration meter 80 in a sufficiently wet state even after a state in which no medicinal solution is present in the medicinal solution tank 20 is kept for a relatively long period.

For example, the endoscope reprocessor 1 according to the present embodiment makes it possible to take concentration measurements of the medicinal solution using the concentration meter 80 without providing a waiting time after the medicinal solution in the medicinal solution tank 20 is replaced.

Also, in the present embodiment, for example, when water is used as the preserving fluid 79, ions which are to be measured by the concentration meter 80 do not get into the content fluid 83 of the concentration meter 80, and thus an impact of immersion of the measuring surface 82 in the preserving fluid 79 on results of concentration measurements can be curbed. For example, when the medicinal solution is a peracetic acid solution and the preserving fluid 79 is water, because the molecular weight of peracetic acid in the content fluid 83 can be reduced as the measuring unit 81 is caused to be held by the second detachable portion 71 and the measuring surface 82 is immersed in the preserving fluid 79, a next concentration measurement can be started without waiting for the molecular weight of peracetic acid in the content fluid 83 to fall.

Also, in the present embodiment, if, for example, a cleaning solution or disinfecting solution is used as the preserving fluid 79, the preserving fluid tank 70 can be kept clean.

Also, in the present embodiment, if, for example, a high polarity liquid is used as the preserving fluid 79, the measuring surface 82 can be kept in a state of being covered with the high polarity liquid when the measuring unit 81 is removed from the second detachable portion 71. Consequently, when the measuring unit 81 is moved from the second detachable portion 71 to the first detachable portion 60, even if oil or the like floats on a surface of the medicinal solution in the medicinal solution tank 20, the presence of the high polarity liquid prevents contact between the measuring surface 82 and oil.

Figure 4:
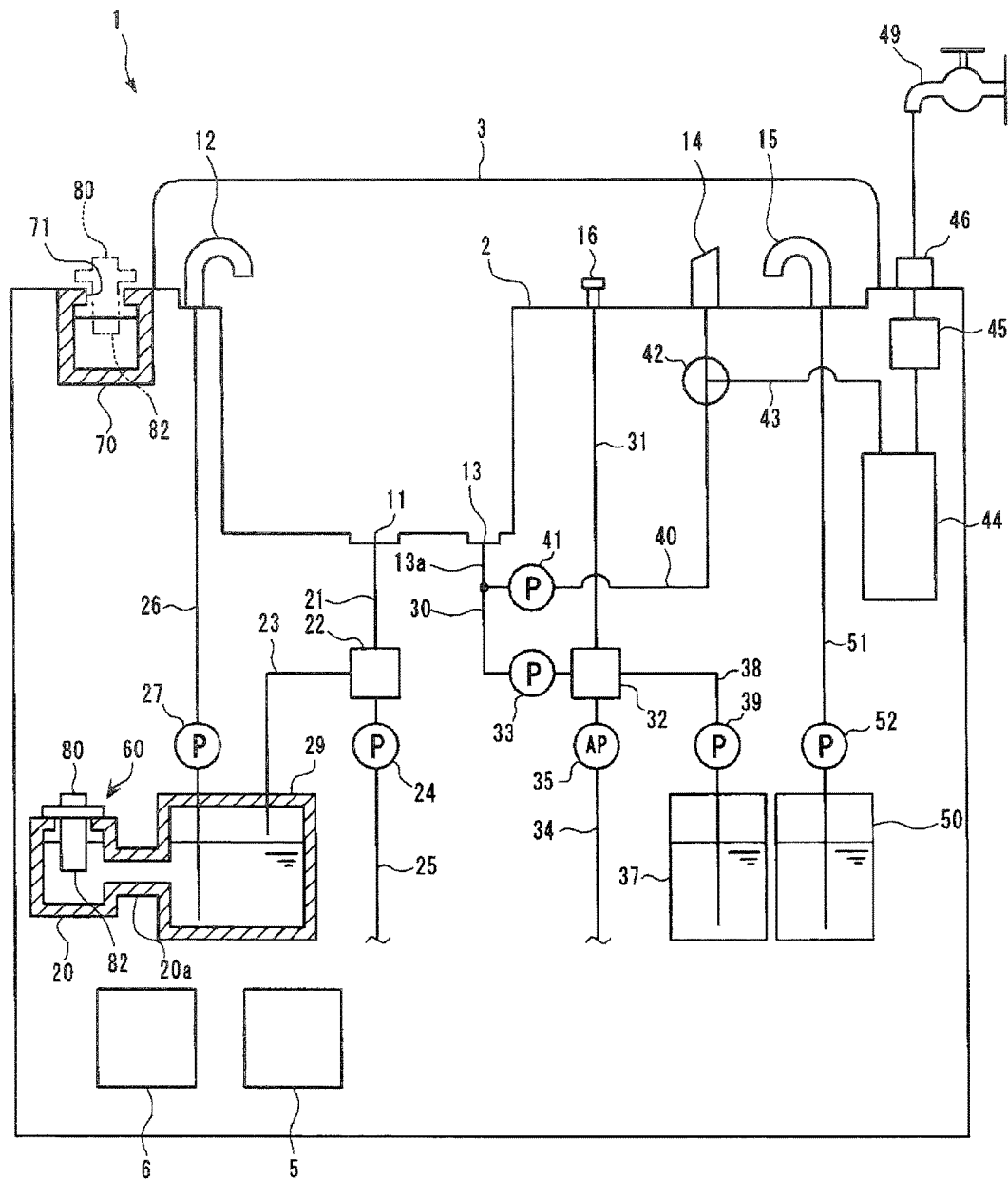
FIG. 4 is a diagram showing a schematic configuration of an endoscope reprocessor according to a first modification of the first embodiment.

A first modification of the endoscope reprocessor 1 according to the present embodiment is shown in FIG. 4. The present modification shown in FIG. 4 differs from the embodiment described above in that the medicinal solution tank 20 and medicinal solution recovery unit 29 are provided separately from each other. The rest of the components are the same as the components in the embodiment described above. A medicinal solution tank 20 according to the present modification communicates with the medicinal solution recovery unit 29 through one or more connection conduits 20a. Therefore, according to the present modification, the liquid level of the medicinal solution stored in the medicinal solution tank 20 becomes equal to height of the medicinal solution stored in the medicinal solution recovery unit 29.

Note that the connection conduit 20a may be provided with a pump configured to transfer the medicinal solution between the medicinal solution tank 20 and medicinal solution recovery unit 29. By causing the medicinal solution to move back and forth between the medicinal solution tank 20 and medicinal solution recovery unit 29 using a pump provided on the connection conduit 20a, it is possible to prevent imbalance in the concentration of the medicinal solution between inner part of the medicinal solution tank 20 and the medicinal solution recovery unit 29.

Figure 5:
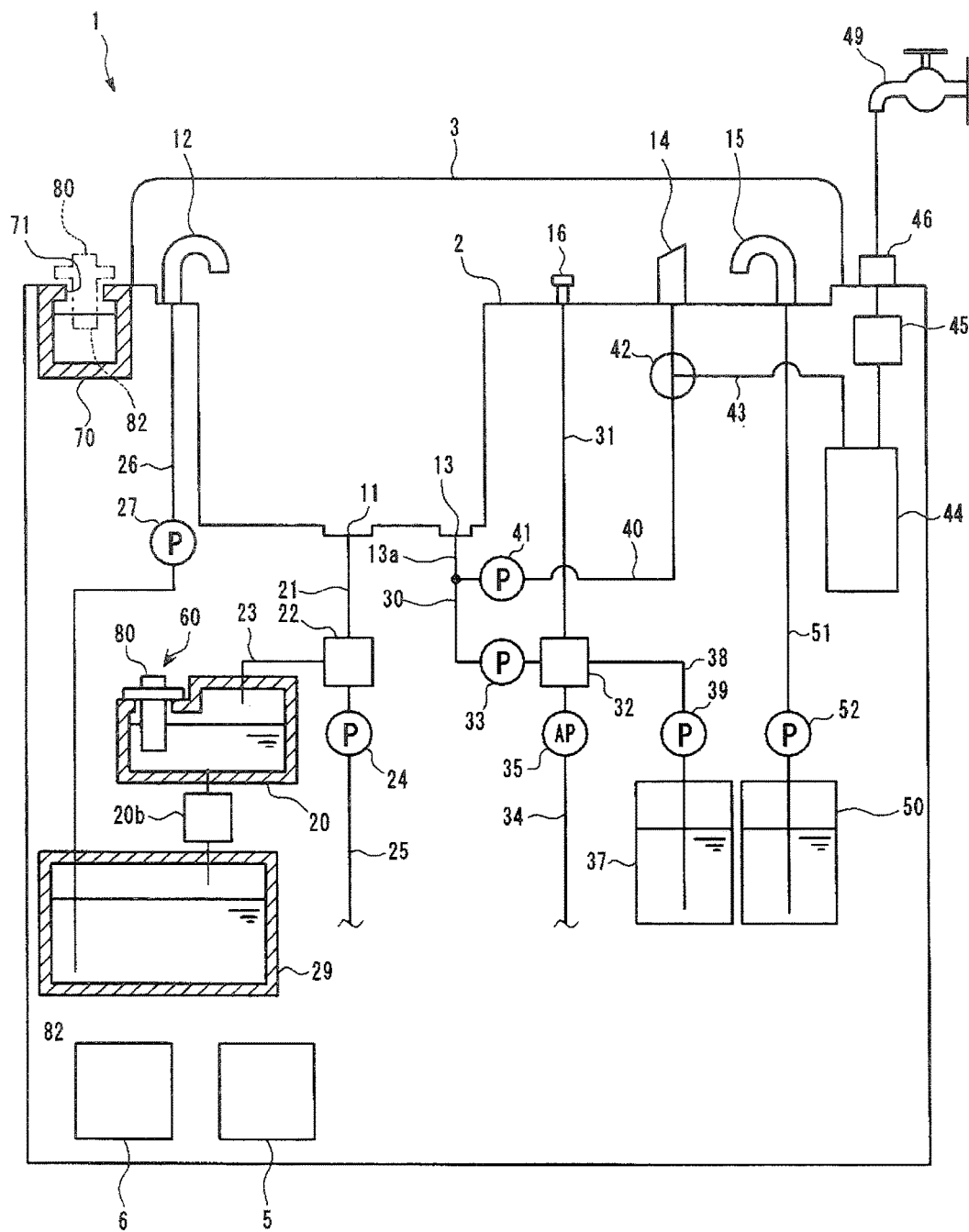
FIG. 5 is a diagram showing a schematic configuration of an endoscope reprocessor according to a second modification of the first embodiment.

A second modification of the endoscope reprocessor 1 according to the present embodiment is shown in FIG. 5. The present modification shown in FIG. 5 differs from the embodiment described above in that the medicinal solution tank 20 and medicinal solution recovery unit 29 are provided separately from each other. The rest of the components are the same as the components in the embodiment described above. A medicinal solution tank 20 according to the present modification is provided halfway along the recovery conduit 23. Also, an on-off valve 20b is provided in a section of the recovery conduit 23 between the medicinal solution tank 20 and medicinal solution recovery unit 29.

According to the present modification, when the medicinal solution is stored in the treatment tank 2, if the selector valve 22 is set such that the discharge conduit 21 and recovery conduit 23 communicate with each other and the on-off valve 20b is closed, the medicinal solution is transferred from the treatment tank 2 to the medicinal solution tank 20. In this state, the measuring surface 82 of the concentration meter 80 is submerged in the medicinal solution, allowing concentration measurements of the medicinal solution to be taken using the concentration meter 80. In performing a reprocessing process for the endoscope, the on-off valve 20b is opened to transfer the medicinal solution from the medicinal solution tank 20 to the medicinal solution recovery unit 29.

(Second Embodiment)

Next, a second embodiment of the present invention will be described. Differences from the first embodiment will only be described below, wherein components similar to those of the first embodiment are denoted by the same reference numerals as the corresponding components, and description of the components will be omitted as appropriate.

Figure 6:
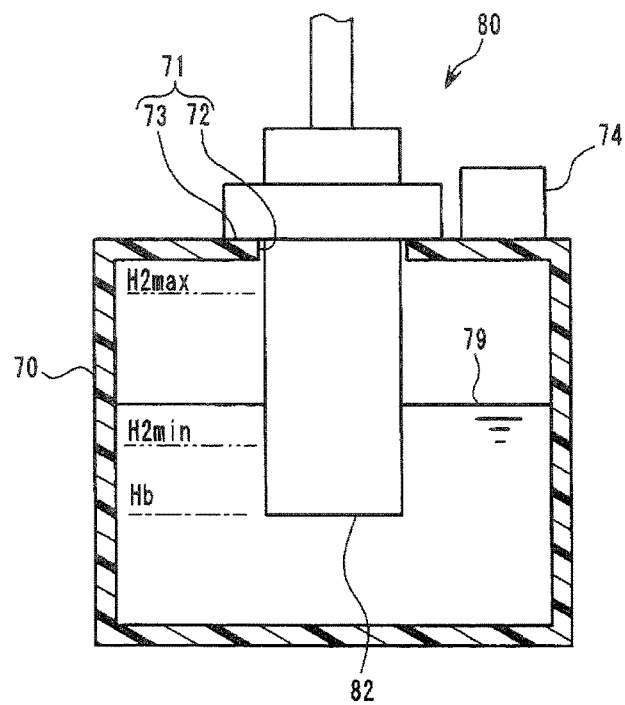
FIG. 6 is a diagram showing a schematic configuration of a preserving fluid tank according to a second embodiment.

FIG. 6 is a diagram showing a schematic configuration of the preserving fluid tank 70 according to the present embodiment. As shown in FIG. 6, the endoscope reprocessor 1 according to the present embodiment includes a concentration meter information readout unit 74. The concentration meter information readout unit 74 detects whether or not the second detachable portion 71 is holding the concentration meter 80 and outputs detection results to the control unit 5.

A configuration of the concentration meter information readout unit 74 is not particularly limited. For example, the concentration meter information readout unit 74 may be a contact switch, output information of which changes with presence or absence of contact with the concentration meter 80 held by the second detachable portion 71. Also, for example, the concentration meter information readout unit 74 may be a proximity sensor, output information of which changes with presence or absence of the concentration meter 80 held by the second detachable portion 71, in proximity. Also, for example, the concentration meter information readout unit 74 may be configured to detect whether or not the second detachable portion 71 is holding the concentration meter 80 based on whether or not communication can be established with a RFID tag of the concentration meter 80.

The endoscope reprocessor 1 can regulate, drive, or stop various functions of the endoscope reprocessor 1 as well based on readout results produced by the concentration meter information readout unit 74. For example, when it is detected by the concentration meter information readout unit 74 that the second detachable portion 71 is holding the concentration meter 80, the endoscope reprocessor 1 according to the present embodiment can shift to a waiting state in which power supply to various components is limited or cut off. Even in the waiting state, the concentration meter information readout unit 74 continues to operate.

For example, when it is detected by the concentration meter information readout unit 74 that the second detachable portion 71 is not holding the concentration meter 80, the endoscope reprocessor 1 starts supplying electric power to the various components and shifts to an operating state. In other words, using a readout function of the concentration meter information readout unit 74, attachment and detachment of the concentration meter 80 to and from the second detachable portion 71 can be interlocked with activation and deactivation a main power supply of the endoscope reprocessor 1.

Note that also in the endoscope reprocessor 1 according to the present embodiment, as with the first embodiment, when a state in which no medicinal solution is present in the medicinal solution tank 20 is kept for a relatively long period, as the measuring unit 81 of the concentration meter 80 is caused to be held by the second detachable portion 71, the measuring surface 82 of the concentration meter 80 can be kept in a wet state which allows concentration measurements to be taken promptly.

(Third Embodiment)

Next, a third embodiment of the present invention will be described. Differences from the first and second embodiments will only be described below, wherein components similar to those of the first and second embodiments are denoted by the same reference numerals as the corresponding components, and description of the components will be omitted as appropriate.

Figure 7:
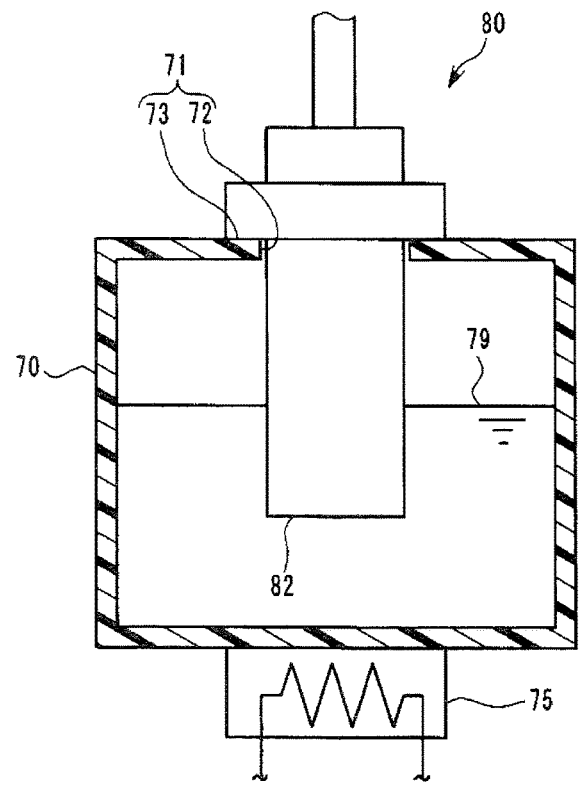
FIG. 7 is a diagram showing a schematic configuration of a preserving fluid tank according to a third embodiment.

FIG. 7 is a diagram showing a schematic configuration of the preserving fluid tank 70 according to the present embodiment. As shown in FIG. 7, the endoscope reprocessor 1 according to the present embodiment includes a temperature regulation unit 75 configured to regulate and thereby keep temperature of the preserving fluid 79 within a predetermined range.

The temperature regulation unit 75 includes any of a component configured to warm the preserving fluid 79, a component configured to cool the preserving fluid 79, a combination of a component configured to warm the preserving fluid 79 and a component configured to cool the preserving fluid 79. Examples of the component configured to warm the preserving fluid 79 include a heating wire and a microwave transmission unit. Also, examples of the component configured to cool the preserving fluid 79 include a Peltier element, a water-cooled tube, and an air-cooled tube.

When the preserving fluid 79 is temperature-regulated directly, for example, with the temperature regulation unit 75 placed inside the preserving fluid tank 70, the preserving fluid tank 70 may be made of a heat insulating material. When the temperature regulation unit 75 temperature-regulates the preserving fluid via the preserving fluid tank 70 as shown in FIG. 7, the preserving fluid tank 70 and temperature regulation unit 75 may be covered with a heat insulating material.

The temperature regulation unit 75 may be either designed to operate under control of the control unit 5 or designed to operate under control of a control unit different from the control unit 5. Also, the operating power of the temperature regulation unit 75 may be designed to be supplied directly from the power supply unit 6, designed to be supplied from a secondary battery connected to the power supply unit 6, or designed to be supplied from a power supply independent of the power supply unit 6.

According to the present embodiment shown in FIG. 7, as an example, the temperature regulation unit 75 includes a heating wire configured to warm the preserving fluid 79 in the preserving fluid tank 70 and keeps the temperature of the preserving fluid 79 in the preserving fluid tank 70 within a predetermined range. Operation of the temperature regulation unit 75 according to the present embodiment may be controlled by a thermostat or may be controlled based on an output from a temperature sensor unit configured to measure the temperature of the preserving fluid 79 in the preserving fluid tank 70.

The predetermined temperature range is equal to a temperature range of the medicinal solution stored in the medicinal solution tank 20. Therefore, according to the present modification, with the measuring unit 81 of the concentration meter 80 caused to be held by the second detachable portion 71, temperature of the content fluid 83 can be kept within the temperature range of the medicinal solution stored in the medicinal solution tank 20.

This makes it possible to reduce a temperature difference between the content fluid 83 and medicinal solution after the measuring unit 81 is moved from the second detachable portion 71 to the first detachable portion 60 and thereby reduce measurement error of the concentration meter 80 in measuring the concentration of the medicinal solution.

Note that a period during which the temperature regulation unit 75 regulates the temperature of the preserving fluid 79 is not particularly limited. For example, the endoscope reprocessor 1 may be designed to always regulate the temperature of the preserving fluid 79 using the temperature regulation unit 75.

Also, for example, the endoscope reprocessor 1 may be designed to start regulating the temperature of the preserving fluid 79 using the temperature regulation unit 75 at a time when the concentration meter 80 is removed from the first detachable portion 60 or at a time when the concentration meter 80 is held by the second detachable portion 71. For example, when the endoscope reprocessor 1 includes the concentration meter information readout unit 74 as with the second embodiment, the control unit 5 starts regulating the temperature of the preserving fluid 79 using the temperature regulation unit 75 at a time when it is judged, based on output information from the concentration meter information readout unit 74, that the concentration meter 80 is held by the second detachable portion 71.

Also, for example, the endoscope reprocessor 1 may be designed to start regulating the temperature of the preserving fluid 79 using the temperature regulation unit 75 after a lapse of a predetermined time from a time point at which the concentration meter 80 is removed from the first detachable portion 60 or after a lapse of a predetermined time from a time point at which the concentration meter 80 is held by the second detachable portion 71.

Also, for example, the endoscope reprocessor 1 may be designed to start regulating the temperature of the preserving fluid 79 using the temperature regulation unit 75 from a date and time set in advance. Here, the date and time set in advance is, for example, information inputted by the user in advance, such as a predetermined time before a date and time when the endoscope reprocessor 1 is scheduled to be used. Note that the control unit 5 may be provided with a calendar function for determining a day of the week and configured to estimate and set a date and time to start regulating the temperature of the preserving fluid 79 using the temperature regulation unit 75, based on a past usage pattern of the endoscope reprocessor 1.

Note that also in the endoscope reprocessor 1 according to the present embodiment as with the first and second embodiments, when a state in which no medicinal solution is present in the medicinal solution tank 20 is kept for a relatively long period, as the measuring unit 81 of the concentration meter 80 is caused to be held by the second detachable portion 71, the measuring surface 82 of the concentration meter 80 can be kept in a wet state which allows concentration measurements to be taken promptly.

(Fourth Embodiment)

Next, a fourth embodiment of the present invention will be described. Differences from the first to third embodiments will only be described below, wherein components similar to those of the first to third embodiments are denoted by the same reference numerals as the corresponding components, and description of the components will be omitted as appropriate.

Figure 8:
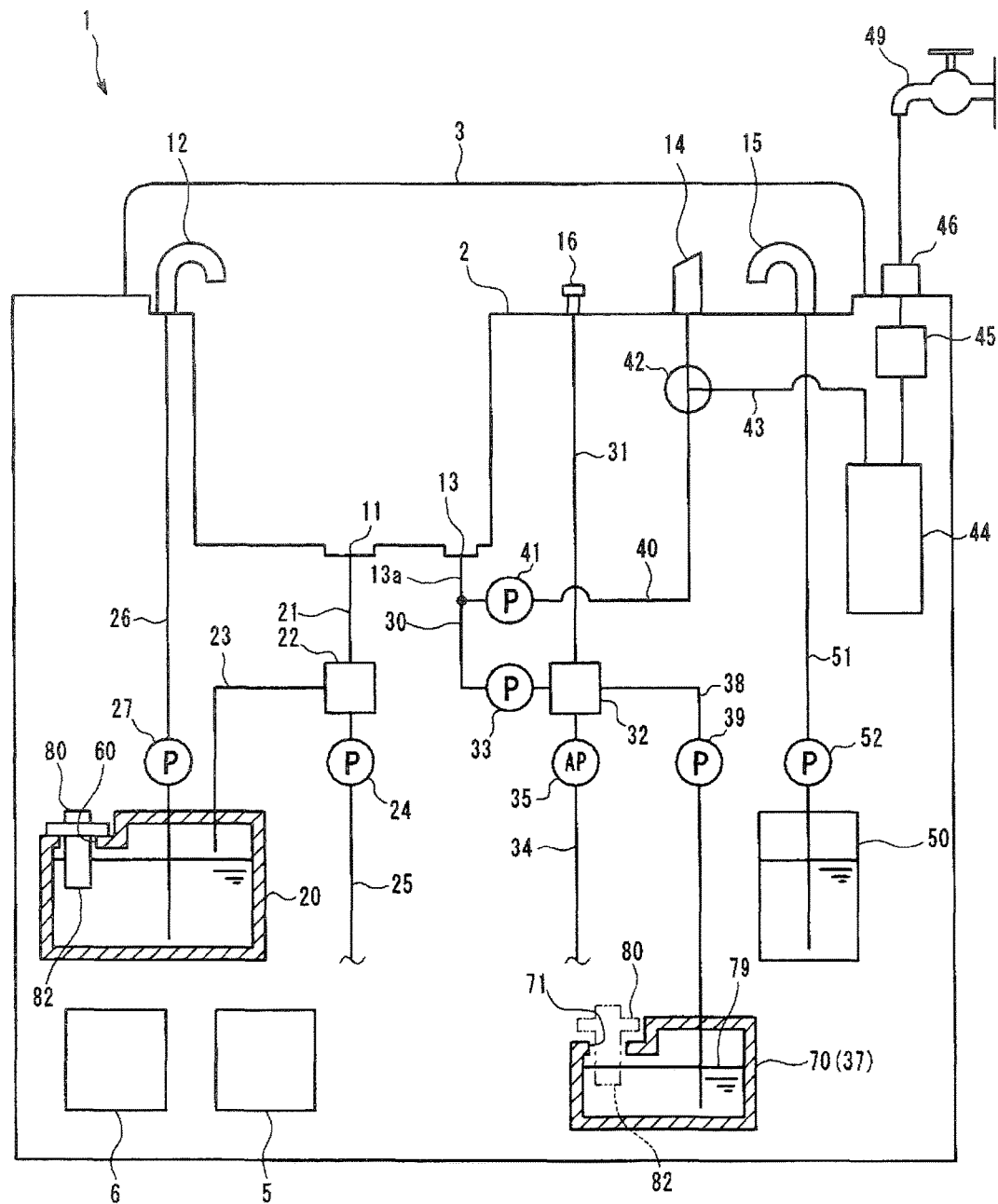
FIG. 8 is a diagram showing a schematic configuration of an endoscope reprocessor according to a fourth embodiment.

The endoscope reprocessor 1 according to the present embodiment shown in FIG. 8 differs from the first to third embodiments described above in that the preserving fluid tank 70 also serves as an alcohol tank 37. That is, according to the present embodiment, the preserving fluid 79 is alcohol. Examples of the alcohol include ethanol. Alcohol concentration can be selected appropriately.

Figure 9:
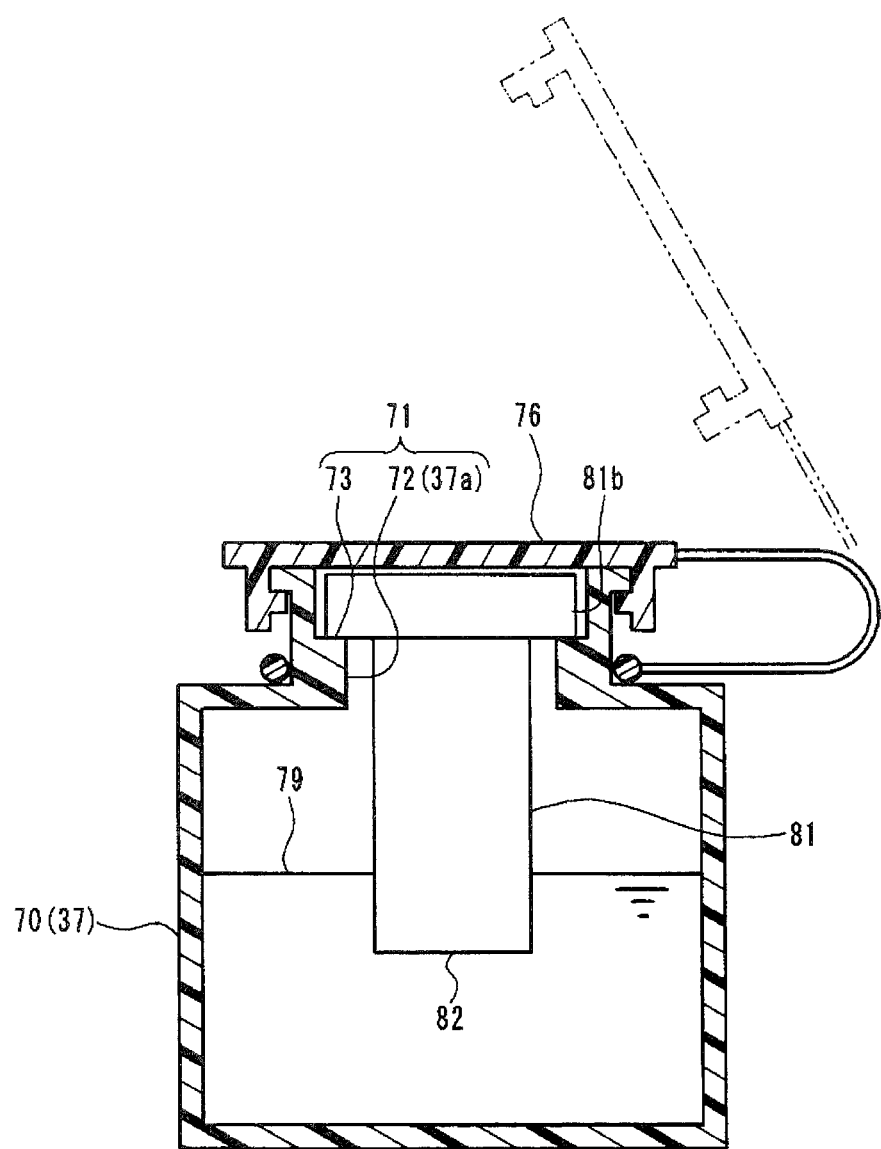
FIG. 9 is a sectional view of a preserving fluid tank and a second detachable portion according to the fourth embodiment.

As shown in FIG. 9, according to the present embodiment, as an example, the insertion hole 72 of the second detachable portion 71 also serves, for example, as a fill port 37a used to inject alcohol into the alcohol tank 37. The insertion hole 72 is provided with a lid member 76 configured to seal the insertion hole 72. The lid member 76 can seal the insertion hole 72 regardless of whether the second detachable portion 71 is holding the concentration meter 80. The lid member 76 prevents scattering and vaporization of alcohol which is the preserving fluid 79.

Note that the insertion hole 72 of the second detachable portion 71 may be designed to also serve as an opening portion through which an alcohol conduit 38 used to lead out alcohol from the alcohol tank 37 is inserted.

According to the present embodiment, as an example, the holding portion 73 of the second detachable portion 71 is a stepped portion provided in the insertion hole 72. When the measuring unit 81 is inserted into the insertion hole 71 by a predetermined distance, the holding portion 73 abuts the convex portion 81b projecting from the lateral portion of the measuring unit 81 and thereby limits a further advance of the measuring unit 81 into the insertion hole 71.

Also in the endoscope reprocessor 1 according to the present embodiment, as with the first to third embodiments, when a state in which no medicinal solution is present in the medicinal solution tank 20 is kept for a relatively long period, as the measuring unit 81 of the concentration meter 80 is caused to be held by the second detachable portion 71, the measuring surface 82 of the concentration meter 80 can be kept in a wet state which allows concentration measurements to be taken promptly.

Figure 10:
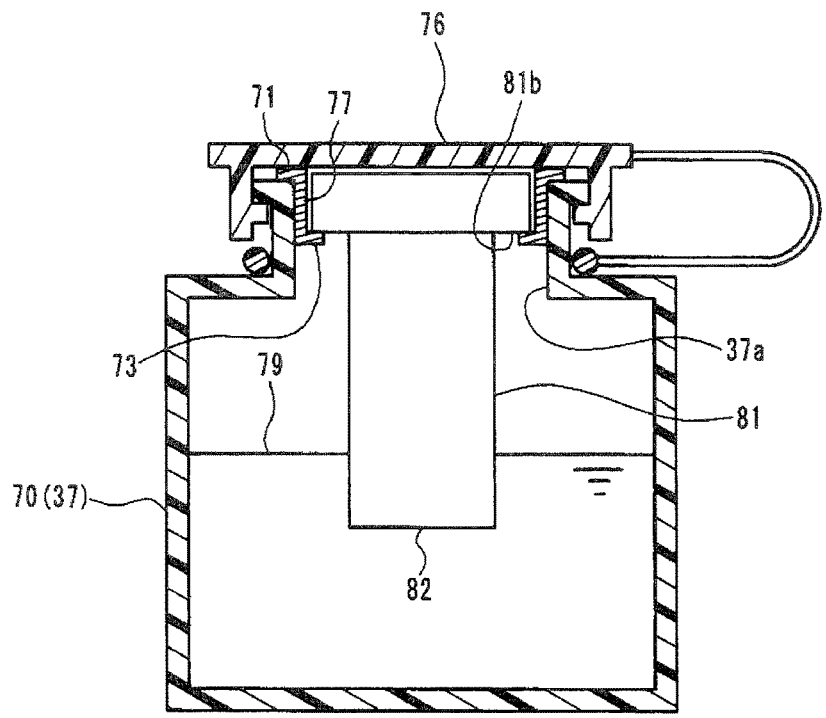
FIG. 10 is a sectional view showing a first modification of the second detachable portion according to the fourth embodiment.

A first modification of the second detachable portion 71 according to the present embodiment is shown in FIG. 10. The modification shown in FIG. 10 differs from the embodiment described above in that the second detachable portion 71 is made of a member different from the member included in the preserving fluid tank 70. The rest of the components are the same as the components in the embodiment described above.

The second detachable portion 71 according to the present modification is a member fitted in the fill port 37a of the alcohol tank 37. The second detachable portion 71 according to the present modification includes a cylindrical fitting portion 77 configured to fit in the fill port 37a at a predetermined position and a holding portion 73 configured to project radially inward from an inner circumferential surface of the fitting portion 77.

When the measuring unit 81 is inserted into the fill port 37a by a predetermined distance, the holding portion 73 abuts the convex portion 81b projecting from the lateral portion of the measuring unit 81 and thereby limits a further advance of the measuring unit 81 into the fill port 37a.

The second detachable portion 71 according to the first modification configured as described above allows the second detachable portion 71 to be provided on the alcohol tank 37, which is the preserving fluid tank 70, without changing a shape of the existing alcohol tank 37.

Figure 11:
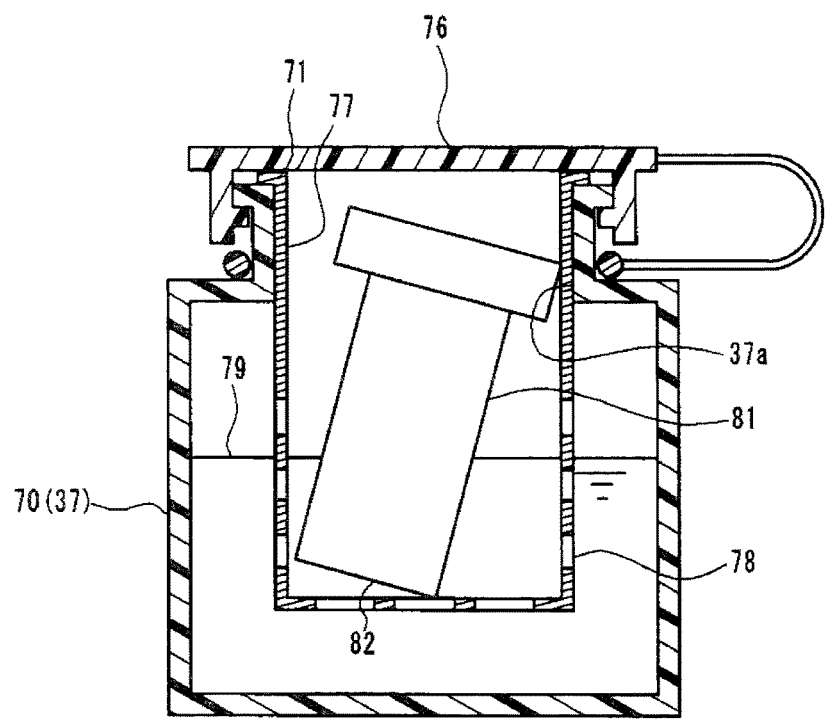
FIG. 11 is a sectional view showing a second modification of the second detachable portion according to the fourth embodiment.

A second modification of the second detachable portion 71 according to the present embodiment is shown in FIG. 11. The modification shown in FIG. 11 differs from the embodiment described above in that the second detachable portion 71 is made of a member different from the member included in the preserving fluid tank 70. The rest of the components are the same as the components in the embodiment described above.

The second detachable portion 71 according to the present modification is a member inserted into the fill port 37a of the alcohol tank 37. The second detachable portion 71 according to the present modification includes a cylindrical fitting portion 77 configured to fit in the fill port 37a at a predetermined position and a netlike portion 78 configured to project from the fitting portion 77 into the alcohol tank 37.

The netlike portion 78 has a bottomed bag shape or cylindrical shape and a bottom portion of the netlike portion 78 is submerged below the liquid surface of the preserving fluid 79 in the alcohol tank 37. The netlike portion 78 is provided with plural through-holes configured to transmit the preserving fluid 79. The measuring unit 81 of the concentration meter 80 can be housed inside the netlike portion 78. The measuring unit 81 housed inside the netlike portion 78 is held at a predetermined position at which the measuring surface 82 is submerged in the preserving fluid 79.

The second detachable portion 71 according to the second modification configured as described above allows the second detachable portion 71 to be provided on the alcohol tank 37, which is the preserving fluid tank 70, without changing a shape of the existing alcohol tank 37 as with the first modification.

(Fifth Embodiment)

Next, a fifth embodiment of the present invention will be described. Differences from the first to third embodiments will only be described below, wherein components similar to those of the first to third embodiments are denoted by the same reference numerals as the corresponding components, and description of the components will be omitted as appropriate.

Figure 12:
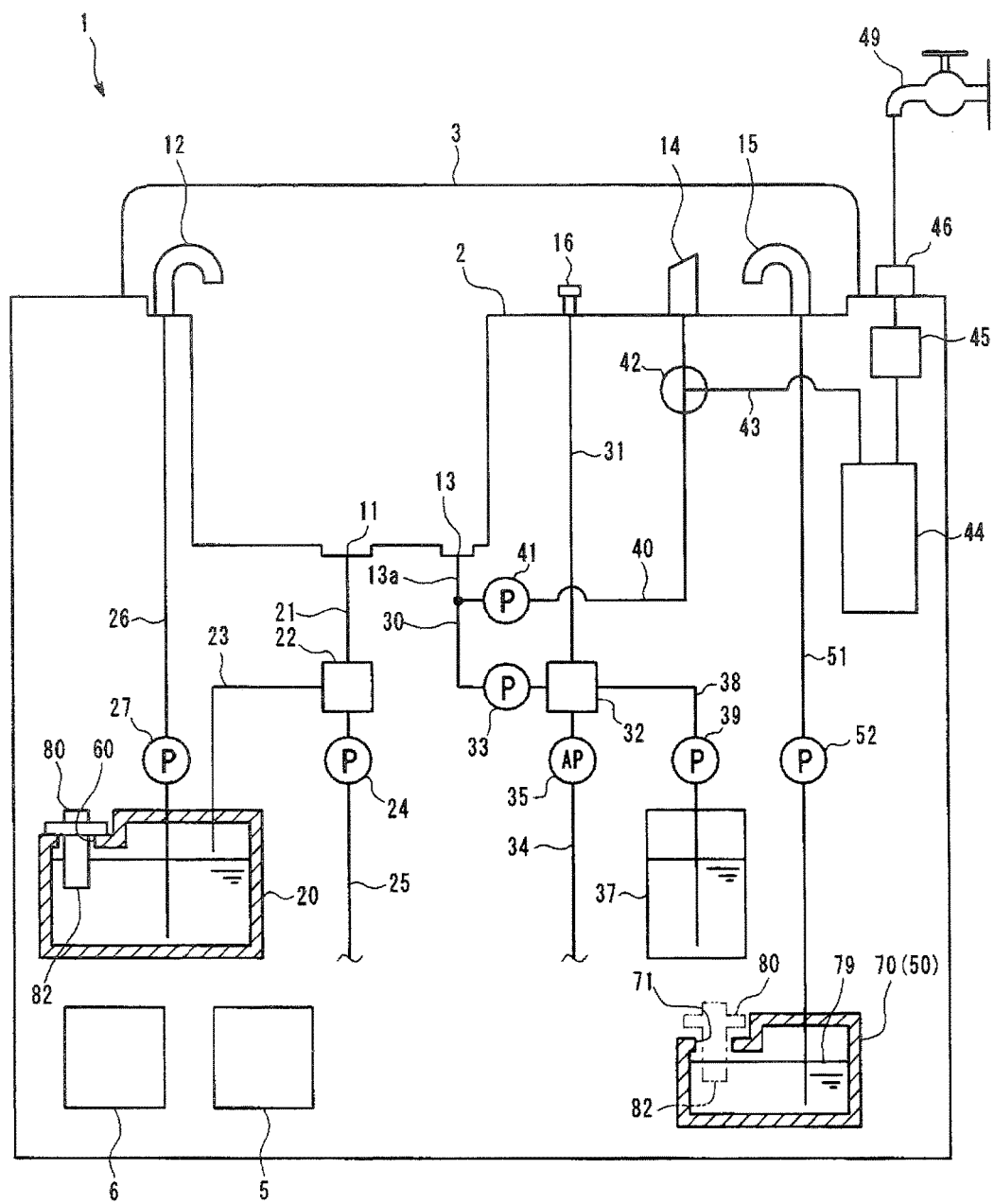
FIG. 12 is a diagram showing a schematic configuration of an endoscope reprocessor according to a fifth embodiment.

The endoscope reprocessor 1 according to the present embodiment shown in FIG. 12 differs from the first to third embodiment described above in that the preserving fluid tank 70 also serves as the cleaning solution tank 50. That is, according to the present embodiment, the preserving fluid 79 is a cleaning solution.

Figure 13:
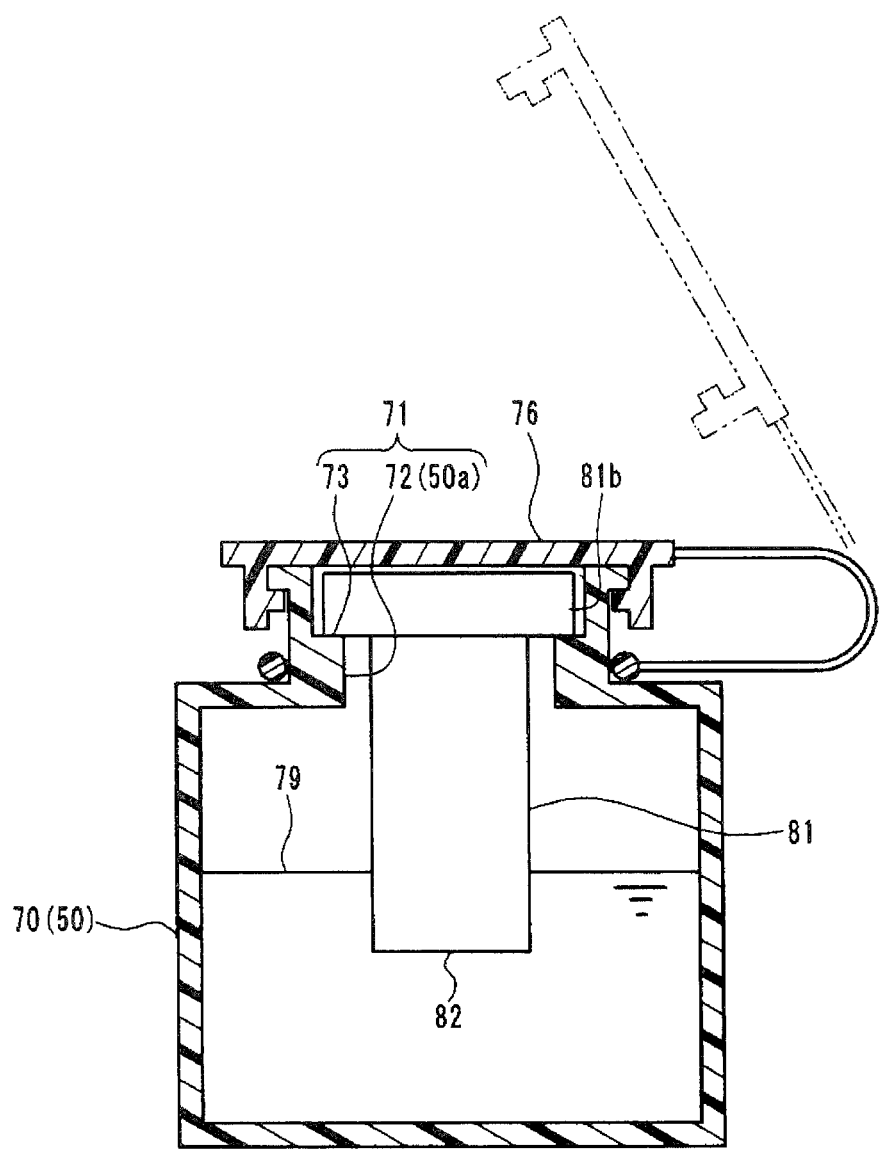
FIG. 13 is a sectional view of a preserving fluid tank and a second detachable portion according to the fifth embodiment.

As shown in FIG. 13, according to the present embodiment, as an example, the insertion hole 72 of the second detachable portion 71 also serves, for example, as a fill port 50a used to inject the cleaning solution into the cleaning solution tank 50. The insertion hole 72 is provided with a lid member 76 configured to seal the insertion hole 72. The lid member 76 can seal the insertion hole 72 regardless of whether the second detachable portion 71 is holding the concentration meter 80. The lid member 76 prevents scattering and vaporization of the preserving fluid 79, which is a cleaning solution.

Note that the insertion hole 72 of the second detachable portion 71 may be designed to also serve as an opening portion through which the cleaning solution conduit 51 used to lead out the cleaning solution from the cleaning solution tank 50 is inserted.

According to the present embodiment, as an example, the holding portion 73 of the second detachable portion 71 is a stepped portion provided in the insertion hole 72. When the measuring unit 81 is inserted into the insertion hole 61 by a predetermined distance, the holding portion 73 abuts the convex portion 81b projecting from the lateral portion of the measuring unit 81 and thereby limits a further advance of the measuring unit 81 into the insertion hole 61.

Also in the endoscope reprocessor 1 according to the present embodiment, as with the first to third embodiments, when a state in which no medicinal solution is present in the medicinal solution tank 20 is kept for a relatively long period, as the measuring unit 81 of the concentration meter 80 is caused to be held by the second detachable portion 71, the measuring surface 82 of the concentration meter 80 can be kept in a wet state which allows concentration measurements to be taken promptly.

Note that as with the first and second modifications of the fourth embodiment described above, the second detachable portion 71 according to the present embodiment may be made of a member different from the member included in the preserving fluid tank 70.

(Sixth Embodiment)

Next, a sixth embodiment of the present invention will be described. Differences from the first to third embodiments will only be described below, wherein components similar to those of the first to third embodiments are denoted by the same reference numerals as the corresponding components, and description of the components will be omitted as appropriate.

Figure 14:
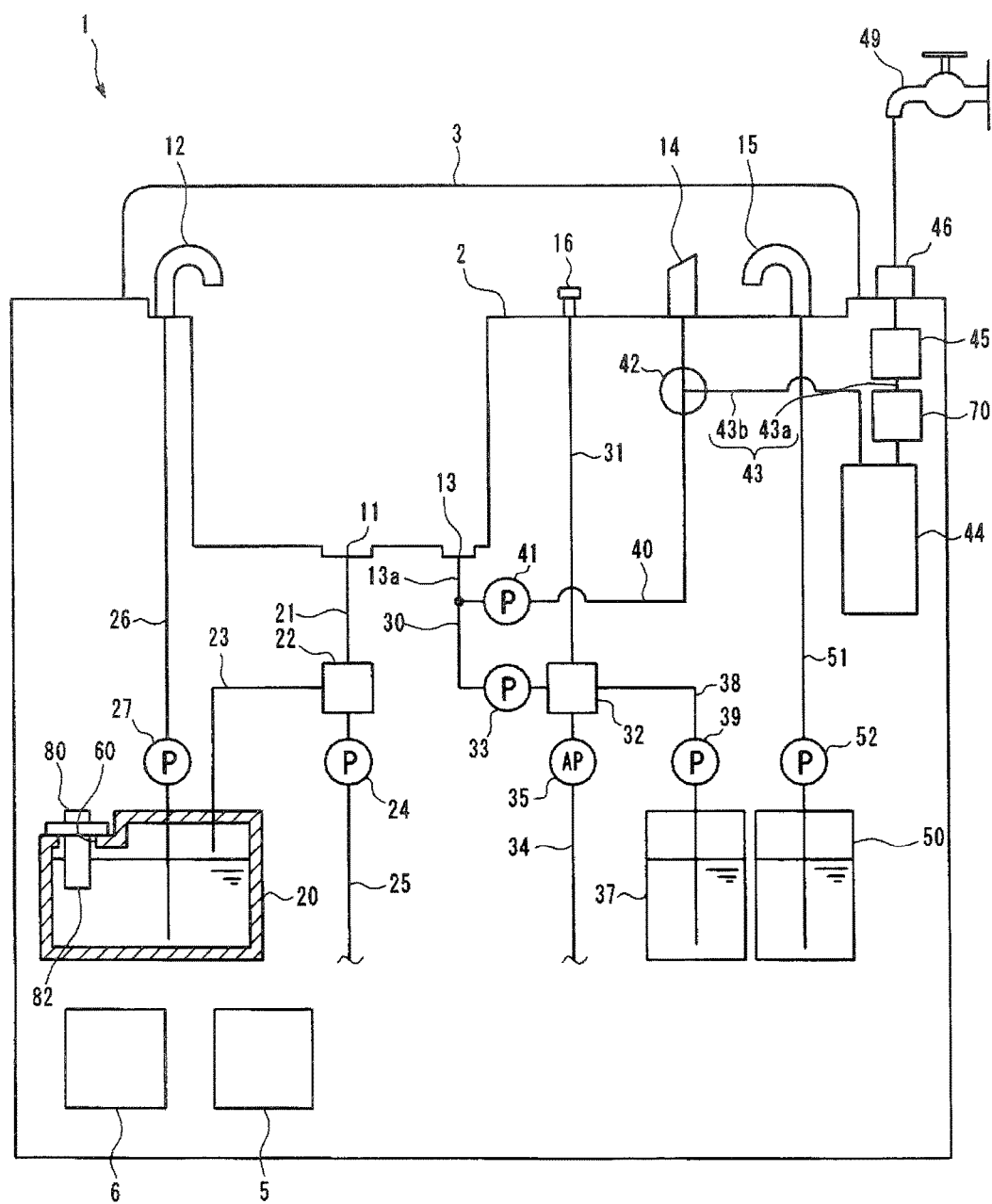
FIG. 14 is a diagram showing a schematic configuration of an endoscope reprocessor according to a fifth embodiment.

The endoscope reprocessor 1 according to the present embodiment shown in FIG. 14 differs from the first to third embodiments in that the preserving fluid tank 70 is provided halfway along a conduit through which a liquid is passed during a reprocessing process for the endoscope.

According to the present embodiment, as an example, the preserving fluid tank 70 is provided on the water supply conduit 43. Of the water supply conduit 43, a section linking the water supply source 49 and water filter 44 is designated as a first water supply conduit 43a and a section linking the water filter 44 and treatment tank 2 is designated as a second water supply conduit 43b. According to the present embodiment, the preserving fluid tank 70 is provided on the first water supply conduit 43a.

Figure 15:
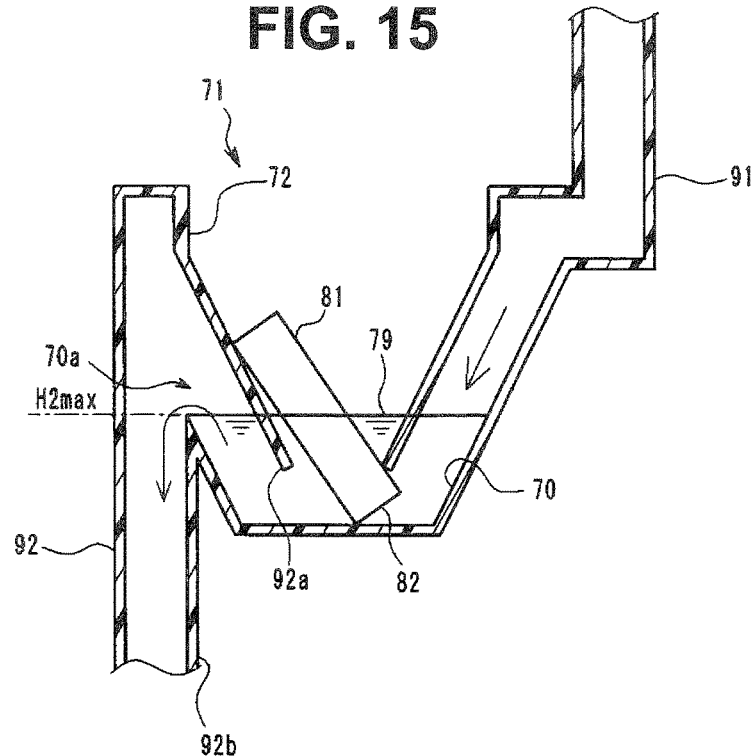
FIG. 15 is a sectional view of a preserving fluid tank and a second detachable portion according to a sixth embodiment.

FIG. 15 is a sectional view of the preserving fluid tank 70 and second detachable portion 71. The preserving fluid tank 70 includes a preserving fluid introduction portion 91 configured to introduce the preserving fluid 79 into the preserving fluid tank 70 and a preserving fluid lead-out portion 92 configured to lead out the preserving fluid 79 from within the preserving fluid tank 70. The preserving fluid introduction portion 91 is connected to an upstream side of the conduit on which the preserving fluid tank 70 is provided. On the other hand, the preserving fluid lead-out portion 92 is connected to a downstream side of the conduit on which the preserving fluid tank 70 is provided.

According to the present embodiment, as an example, the preserving fluid introduction portion 91 is connected to an upstream side of the first water supply conduit 43a. That is, the preserving fluid introduction portion 91 communicates with the water supply source 49 through the first water supply conduit 43a. Also, according to the present embodiment, as an example, the preserving fluid introduction portion 91 is connected to a downstream side of the first water supply conduit 43a. That is, the preserving fluid introduction portion 91 communicates with the water filter 44 through the first water supply conduit 43a.

The preserving fluid introduction portion 91 is placed at such a position that the water discharged from the preserving fluid introduction portion will fall into the preserving fluid tank 70. The preserving fluid lead-out portion 92 is tubular in shape, and a first end portion 92a opens in the preserving fluid tank 70 while a second end portion 92b opens at a lower position in the direction of gravity than the first end portion 92a. Also, a tubular portion linking the first end portion 92a and second end portion 92b of the preserving fluid lead-out portion 92 turns back at a higher position in the direction of gravity than an opening of the first end portion 92a.

When water, which is the preserving fluid 79, is introduced into the preserving fluid tank 70 according to the present embodiment described above through the preserving fluid introduction portion 91, first the water is stored up to a predetermined height H2max. Then, after water is stored up to the predetermined height H2max, if water is further introduced through the preserving fluid introduction portion 91, the water is led out of the preserving fluid tank 70 via the preserving fluid lead-out portion 92.

In this way, the preserving fluid tank 70 according to the present embodiment is a part which stores part of a liquid as a preserving fluid halfway along a conduit through which the liquid is passed during a reprocessing process for the endoscope.

In other words, the preserving fluid tank 70 is a member configured to store a liquid up to the predetermined height H2max when the liquid is introduced from a conduit on an upstream side via the preserving fluid introduction portion 91. The preserving fluid tank 70 is configured such that the liquid will overflow when the liquid level of the stored liquid exceeds the predetermined height H2max. For example, if a spillway portion 70a, which is an opening portion, is provided at the predetermined height H2max in the preserving fluid tank 70 the liquid introduced into the preserving fluid tank 70 overflows from the preserving fluid tank 70 through the spillway portion 70a after being stored up to the predetermined height H2max in the preserving fluid tank 70.

The liquid overflowing from the preserving fluid tank 70 is led to a conduit on a downstream side through the preserving fluid lead-out portion 92. The liquid overflowing from the preserving fluid tank 70 flows upward, and then downward. The tubular shape of the preserving fluid lead-out portion 92 described above is provided along a flow of the liquid overflowing from the preserving fluid tank 70.

Note that shape of the preserving fluid lead-out portion 92 is not limited to the tubular shape. For example, the preserving fluid lead-out portion 92 may be a saucer-shaped container configured to receive the liquid overflowing from the preserving fluid tank 70, below the preserving fluid tank 70.

The preserving fluid tank 70 is provided with the second detachable portion 71. The second detachable portion 71 includes the insertion hole 72 provided above the H2max in the preserving fluid tank 70. As the measuring unit 81 of the concentration meter 80 is inserted into the insertion hole 72, the measuring surface 82 is submerged in water, which is the preserving fluid 79.

Also in the endoscope reprocessor 1 according to the present embodiment, as with the first to third embodiments, when a state in which no medicinal solution is present in the medicinal solution tank 20 is kept for a relatively long period, as the measuring unit 81 of the concentration meter 80 is caused to be held by the second detachable portion 71, the measuring surface 82 of the concentration meter 80 can be kept in a wet state which allows concentration measurements to be taken promptly.

Also, according to the present embodiment, each time the liquid flows through the conduit on which the preserving fluid tank 70 is provided, the preserving fluid 79 in the preserving fluid tank 70 is replaced. This eliminates the need for an operation of injecting the preserving fluid 79 into the preserving fluid tank 70 or replacing the preserving fluid 79 as well as an operation of managing volume of the preserving fluid 79 stored in the preserving fluid tank 70.

Note that the conduit on which the preserving fluid tank 70 is provided is not limited to the water supply conduit 43 described above. For example, the preserving fluid tank 70 may be provided on the circulation conduit 13a, discharge conduit 21, medicinal solution conduit 26, alcohol conduit 38, or cleaning solution conduit 51.

Also, as with the second embodiment described above, the endoscope reprocessor 1 according to the present embodiment may include the concentration meter information readout unit 74 configured to detect whether or not the second detachable portion 71 is holding the concentration meter 80 and output detection results to the control unit 5.

Also, as with the third embodiment described above, the endoscope reprocessor 1 according to the present embodiment may include the temperature regulation unit 75 configured to regulate and thereby keep temperature of the preserving fluid 79 within a predetermined range. As with the third embodiment, the temperature regulation unit 75 may be provided in the preserving fluid tank 70 or may be provided in the preserving fluid introduction portion 91. When the temperature regulation unit 75 is provided on the preserving fluid introduction portion 91, the temperature regulation unit 75 regulates the temperature of the liquid, which is the preserving fluid 79, passing through the preserving fluid introduction portion 91.

Figure 16:
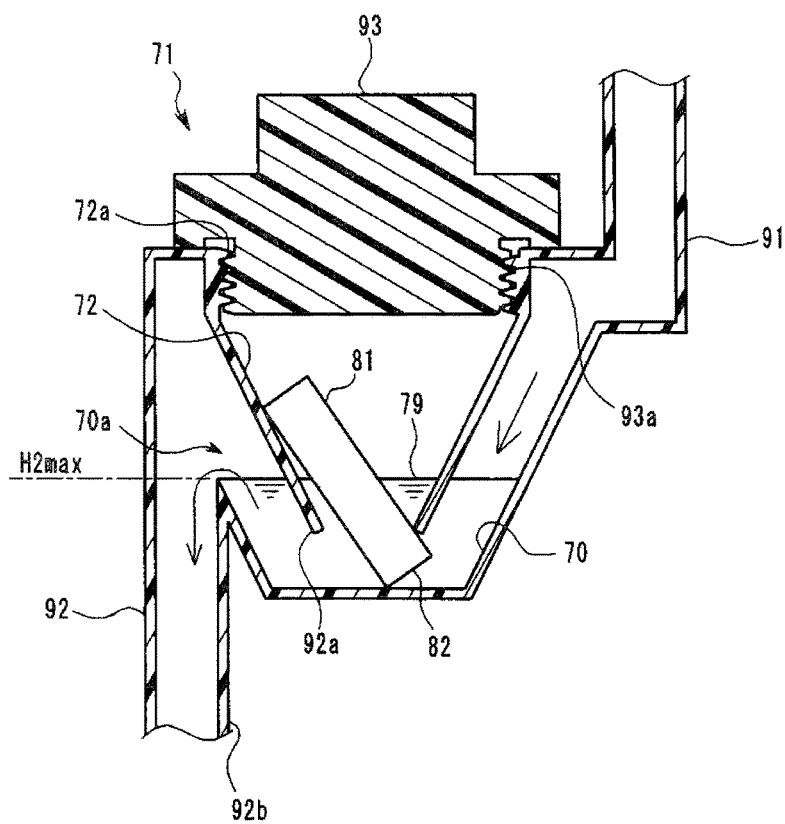
FIG. 16 is a sectional view of the preserving fluid tank and a modification of the second detachable portion according to the sixth embodiment.

A modification of the second detachable portion 71 according to the present embodiment is shown in FIG. 16. The second detachable portion 71 according to the present modification shown in FIG. 16 differs from the embodiment described above in that the second detachable portion 71 includes a lid member 93 configured to seal the insertion hole 72. The rest of the components are the same as the components in the embodiment described above.

The lid member 93 can seal the insertion hole 72 regardless of whether the second detachable portion 71 is holding the concentration meter 80. Also, the lid member 93 is configured to be fixable with the insertion hole 72 sealed. According to the present embodiment, as an example, a female thread portion 72a is formed in an inner circumferential surface of the insertion hole 72 and a male thread portion 93a configured to be screwed into the female thread portion 72a is formed on an outer circumferential surface of the lid member 93. Note that the configuration for fixing the lid member 93 to the insertion hole 72 is not limited to that of the present modification and may be a configuration which uses a snap fit or the like configured to engage the lid member 93 with the insertion hole 72, for example, by an elastic force of the lid member 93.

The lid member 93 provided on the insertion hole 72 prevents scattering and vaporization of the preserving fluid 79. Also, if the lid member 93 is configured to be fixable, it is possible to prevent the lid member 93 from falling off due to pressure changes in the preserving fluid tank 70.

Note that the present invention is not limited to the embodiments described above and may be changed as appropriate without departing from the scope and idea readable from the claims and entire specification and that any endoscope reprocessor resulting from such changes is also included in the technical scope of the present invention.

The present invention can implement an endoscope reprocessor configured to keep a measuring surface of a concentration meter in a sufficiently wet state.

What is claimed is:

1. An endoscope reprocessor comprising:
   a treatment tank for holding an endoscope;
   a medicinal solution tank configured to store a medicinal solution, the medicinal solution tank being fluidically connected to the treatment tank by one or more fluid circuits;
   a first detachable portion provided in the medicinal solution tank and configured to detachably hold a concentration meter such that a measuring surface of the concentration meter is placed in the medicinal solution tank;
   a preserving fluid tank configured to store a preserving fluid of the concentration meter, the preserving fluid tank not being connected to output to or input from the treatment tank so as to be fluidically isolated from the treatment tank; and
   a second detachable portion provided in the preserving fluid tank and configured to detachably hold the concentration meter such that the measuring surface of the concentration meter is placed in the preserving fluid tank.

2. The endoscope reprocessor according to claim 1, further comprising:
   a preserving fluid introduction portion configured to introduce the preserving fluid into the preserving fluid tank; and
   a preserving fluid lead-out portion configured to lead out the preserving fluid from the preserving fluid tank.

3. The endoscope reprocessor according to claim 2, further comprising:
   a water filter configured to filter water;
   a first water supply conduit configured to link a water supply source and the water filter; and
   a second water supply conduit configured to link the water filter and the treatment tank, wherein
   the first water supply conduit includes the preserving fluid introduction portion, the preserving fluid tank, and the preserving fluid lead-out portion.

4. The endoscope reprocessor according to claim 3, wherein
   the preserving fluid introduction portion is placed at such a position that water discharged from the preserving fluid introduction portion falls into the preserving fluid tank;
   the preserving fluid lead-out portion is tubular in shape, a first end portion of the preserving fluid lead-out portion opens in the preserving fluid tank while a second end portion of the preserving fluid lead-out portion opens at a lower position in a direction of gravity than the first end portion, and a tubular portion linking the first end portion and second end portion turns back at a higher position in the direction of gravity than an opening of the first end portion.

5. The endoscope reprocessor according to claim 1, further comprising a temperature regulation unit configured to regulate a temperature of the preserving fluid stored in the preserving fluid tank.

6. The endoscope reprocessor according to claim 1, further comprising the concentration meter.

* * * * *